US009829720B2

(12) United States Patent
De Smet et al.

(10) Patent No.: US 9,829,720 B2
(45) Date of Patent: Nov. 28, 2017

(54) ACTIVE MULTIFOCAL LENS

(71) Applicants: UNIVERSITEIT GENT, Ghent (BE); IMEC VZW, Leuven (BE)

(72) Inventors: Herbert De Smet, Destelbergen (BE); Jelle De Smet, Aalst (BE)

(73) Assignees: Universiteit Gent, Ghent (BE); IMEC VZW, Leuven (BE)

( * ) Notice: Subject to any disclaimer, the term of this patent is extended or adjusted under 35 U.S.C. 154(b) by 0 days.

(21) Appl. No.: 14/902,990

(22) PCT Filed: Jul. 5, 2014

(86) PCT No.: PCT/EP2014/064390
§ 371 (c)(1),
(2) Date: Jan. 5, 2016

(87) PCT Pub. No.: WO2015/001120
PCT Pub. Date: Jan. 8, 2015

(65) Prior Publication Data
US 2016/0143728 A1    May 26, 2016

Related U.S. Application Data

(60) Provisional application No. 61/843,141, filed on Jul. 5, 2013.

(30) Foreign Application Priority Data

Sep. 19, 2013    (EP) .................................... 13185251

(51) Int. Cl.
*G02C 7/02* (2006.01)
*G02C 7/04* (2006.01)
(Continued)

(52) U.S. Cl.
CPC ............ *G02C 7/022* (2013.01); *A61F 2/1618* (2013.01); *A61F 2/1624* (2013.01);
(Continued)

(58) Field of Classification Search
CPC ....... A61F 2/1624; G02B 3/0087; G02B 3/10; G02B 3/00; G02B 3/0081; G02C 7/042;
(Continued)

(56) References Cited

U.S. PATENT DOCUMENTS 8,348,422 B2    1/2013  Pugh et al.
8,348,424 B2    1/2013  Pugh et al.
(Continued)

FOREIGN PATENT DOCUMENTS

WO    2008078320 A2    7/2008
WO    2012036638 A1    3/2012
WO    2012051223 A2    4/2012

OTHER PUBLICATIONS

Extended European Search Report for corresponding European Application No. 13185251.9, dated May 26, 2014.
(Continued)

*Primary Examiner* — Darryl J Collins
(74) *Attorney, Agent, or Firm* — Workman Nydegger

(57) ABSTRACT

An optical lens device has an actively controllable focal length. This device comprises an element with lensing effect comprising a plurality of regions. Each such region has a corresponding refractive power for providing a corresponding focal length distinct from the focal length of at least one other region of this plurality of regions. The device further comprises at least one non-centric addressable optical element integrated in or provided on the element with lensing effect. This at least one addressable optical element is adapted for changing the transmittance of at least one of the plurality of regions in response to a control signal. The
(Continued)

device also comprises a control means for generating the control signal.

13 Claims, 4 Drawing Sheets

(51) Int. Cl.
*G02B 3/00* (2006.01)
*A61F 2/16* (2006.01)
*G02C 7/10* (2006.01)
*G02B 3/10* (2006.01)
*G02F 1/17* (2006.01)

(52) U.S. Cl.
CPC ......... *G02B 3/0081* (2013.01); *G02B 3/0087* (2013.01); *G02B 3/10* (2013.01); *G02C 7/04* (2013.01); *G02C 7/042* (2013.01); *G02C 7/045* (2013.01); *G02C 7/101* (2013.01); *G02F 1/17* (2013.01)

(58) Field of Classification Search
CPC ........ G02C 7/045; G02C 7/101; G02C 7/022; G02C 7/04; G02F 1/17
USPC .............. 351/159.1–159.14, 159.03, 159.09, 351/159.29, 159.55, 159.39
See application file for complete search history.

(56) References Cited

U.S. PATENT DOCUMENTS

| | | | |
|---|---|---|---|
| 2004/0027536 A1* | 2/2004 | Blum | B29D 11/00826 351/159.03 |
| 2004/0169932 A1* | 9/2004 | Esch | A61F 2/16 359/665 |
| 2008/0055541 A1* | 3/2008 | Coulter | G02C 7/16 351/159.45 |
| 2010/0053549 A1 | 3/2010 | Legerton et al. | |

OTHER PUBLICATIONS

International Search Report for corresponding International PCT Application No. PCT/EP2014/064390, dated Aug. 21, 2014.

* cited by examiner

ACTIVE MULTIFOCAL LENS

FIELD OF THE INVENTION

The invention relates to the field of multifocal and varifocal optical lenses. More specifically it relates to an optical lens having an actively controllable focal length, for example for ophthalmic applications.

BACKGROUND OF THE INVENTION

An ophthalmic lens, such as a contact lens or an intraocular lens, provides vision correction by introducing a refractive element into the optical line of sight. A conventional ophthalmic lens may provide a fixed correction of the dioptric power of an eye. For example, an optical design is determined taking into account information gathered from the patient, and the lens is manufactured according to this personalized design, e.g. by cast molding or lathing. The optical qualities of such a conventional lens thus are static once the lens has been formed.

However, many people suffer from presbyopia, which means that they have trouble accommodating of vision, e.g. their eyes have a limited focal range or changing focus between nearby and remote sceneries takes a long time. Presbyopia is common among people above the age of 40-50 and may for example be caused by a decreased elasticity of the intraocular lens used for accommodation of vision. Bifocal or 'progressive' spectacles can provide different dioptric corrections that correct the sight for different viewing distances. This is accomplished by dividing the lenses into juxtaposed zones with different dioptric powers, either with a sharp or a gradual transition between these zones. The desired dioptric power is then selected by moving the line of sight so that it crosses the appropriate zone of the spectacle's lens. However, in a contact lens, since it is in direct contact with the eye, it is not easy to move the line of sight and therefore a multifocal contact lens is not easy to implement. For example, a translational dual focal contact lens is known in the art, in which the wearer can shift the lens upward or downward using eye ball movements in order to select a different dioptric zone in the lens. However, the learning curve of such a lens is very steep and its use is not at all obvious, especially for older people. Furthermore, for intraocular lens implants, shifting the lens with respect to the line of sight may be infeasible.

In order to overcome the limitations of conventional contact lenses, dual focal contact lenses are known in the art. In such dual focal contact lenses, two dioptric powers are simultaneously active, leading to two superimposed images, one focused nearby and one remotely focused. However, this has the disadvantage of vision artefacts, such as halos, ghost vision and reduced contrast. Furthermore, dual focal or multifocal contact lenses are known in the art having a plurality of substantially concentric lens zones with different, possibly alternating lens powers. Although such lenses may also lead to superimposed images focused on different distances, due to the concentric arrangement of the lens zones, the effective lens powers will to a certain degree depend on the diameter of the pupil, although there is some optical distance between the latter and the lens. In bright circumstances the pupil diameter is small and the central part of the lens will determine its effective power. In dim lighting circumstances, the pupil dilates, and the influence of the outer rings will be relatively higher. However, the disadvantage of this approach is that there is no guaranteed relationship between pupil diameter and desired lens power. Furthermore, such lens may also be susceptible to vision artefacts such as halos, ghost vision and reduced contrast.

Another approach known in the art involves a lens with an aspheric front or back surface which provides a smooth transition between different focal points from the middle of the lens towards the edge. In such a design the lens operation is also pupil size dependent to a certain degree. Again, such lenses have the disadvantage of being prone to halos, ghost vision and reduced contrast.

Active lenses are also known in the art. For example, U.S. Pat. No. 8,348,424 discloses an ophthalmic lens with a variable optic portion, which is capable of changing the optical quality of the lens, e.g. a cast molded silicone hydrogel contact lens with an energized variable optic insert. Such variable optic insert can for example comprise a liquid meniscus lens with an electrically conducting fluid and oil capable of changing an optical characteristic of the ophthalmic lens.

Furthermore, U.S. Pat. No. 8,348,422 also discloses an energized ophthalmic lens. Embodiments according to U.S. Pat. No. 8,348,422 may comprise activating components within an ophthalmic lens system in response to an external signal, e.g. an eyelid blink or a pressure signal applied to the lens via the closed eyelid.

SUMMARY OF THE INVENTION

It is an object of embodiments of the present invention to provide efficient and good means for variable focal length control, e.g. for selecting a focus, in a multifocal or varifocal lens. In some embodiments of the present invention, efficient and good means for variable focal length control are obtained even at changing light intensity variations.

It is an advantage of embodiments of the present invention that a solution is provided being substantially insensitive to a diaphragm selection, e.g. to the variable pupil diameter for an ophthalmic contact lens.

It is an advantage of embodiments of the present invention that they can be applied in an optical apparatus such as a photographic camera, for example to enable switching the optical apparatus between different focal distances, e.g. for zooming, without requiring mechanically moving parts such as moving lens groups.

It is an advantage of embodiments of the present invention that they can be applied for human vision correction, for example for implementation in a contact lens or in an implantable lens, e.g. an intra-ocular lens.

It is an advantage of embodiments of the present invention that correction of the vision can be obtained that are less or not prone to image artefacts such as halos, ghost vision and reduced contrast.

The above objective is accomplished by a method and device according to the present invention.

It is an advantage of embodiments of the present invention that simple and efficient focus control is provided for ophthalmic lenses, e.g. for a contact lens or intra-ocular lens.

The present invention relates to an optical lens device having an actively controllable focal length, comprising an element with lensing effect comprising a plurality of regions, each region having a corresponding refractive power for providing a corresponding focal length distinct from the focal length of at least one other region of said plurality of regions, at least one addressable optical element integrated in or provided on the element with lensing effect, the at least one addressable optical element being adapted for changing the transmittance of at least one of said plurality of regions in response to a control signal, and a control means for generating said control signal.

The at least one addressable optical element may be a non-concentric area. The non-concentric area may be a non circle-symmetric sector of the optical element with lensing effect. The non-concentric area may comprise one or more sector regions of the optical element with lensing effect. The one or more sector regions may be pie-slice shaped, e.g. having their pie-point in the center of the optical element with lensing effect. The optical lens device may be adapted for use as an ophthalmic contact lens or an intra-ocular implant.

The shape and arrangement of the at least one addressable optical element may be determined by the shape and arrangement of the plurality of regions of the element with lensing effect.

A corresponding addressable optical element may be provided in or on each of said plurality of regions.

The element with lensing effect may be made of rigid gas permeable or soft material.

The at least one addressable optical element may comprise an addressable optical element configured as a sector of the element with lensing effect.

The at least one addressable optical element may cover an area which is substantially less than the total area of the element with lensing effect.

The at least one addressable optical element may comprise overlapping layers.

The at least one addressable optical element may comprise a liquid crystal technology element.

The at least one addressable optical element may comprise a bistable or multistable element.

The at least one addressable optical element may comprise an energy supply.

The present invention also relates to a method for controlling the focal length of an optical lens device, comprising providing an element with lensing effect comprising a plurality of regions, each region having a corresponding refractive power for providing a corresponding focal length distinct from the focal length of at least one other region of said plurality of regions, and changing the transmittance of at least one of said plurality of regions by controlling at least one non-concentric addressable optical element integrated in or provided on the element with lensing effect.

The present invention also relates to the use of an optical lens device as described above for human vision correction.

In another aspect, the present invention relates to an optical lens device having an actively controllable focal length, comprising an element with lensing effect comprising a plurality of regions, each region having a corresponding refractive power for providing a corresponding focal length distinct from the focal length of at least one other region of said plurality of regions, at least one addressable optical element integrated in or provided on the element with lensing effect, the at least one addressable optical element being adapted for changing the transmittance of at least one of said plurality of regions in response to a control signal, and a control means for generating said control signal, the at least one addressable optical element having a lens surface area being at least 10%, e.g at least 15%, e.g. at least 20% of the surface area of the optical element with lensing effect.

According to embodiments of this aspect of the present invention, the at least one addressable optical element integrated in or provided on the element with lensing effect may have any suitable shape such as one or more sectors, concentric, disk shaped.

The optical system may furthermore comprise one or more features corresponding with features of an optical system as described for the first aspect.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
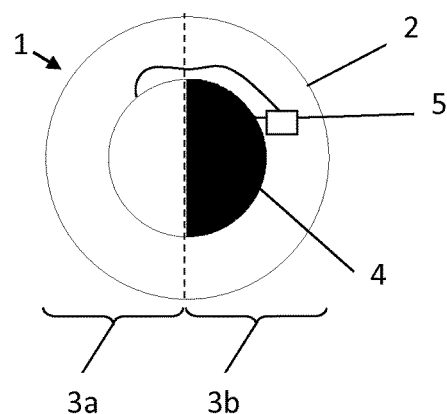
FIG. 1 shows a frontal view of an optical lens device according to embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to an optical lens device, reference may be made to an optical device having a lensing effect, for example a refractive element, a diffractive element or a Fresnel element. The optical lens device may provide controlled scattering.

In a first aspect, the present invention relates to an optical lens device having an actively controllable focal length. The optical lens device comprises an optical element with lensing effect which comprises a plurality of regions. Each such region has a corresponding lensing power for providing a corresponding focal length distinct from the focal length of at least one other region of the plurality of regions. The optical lens device also comprises at least one addressable optical element integrated in or provided on the element with lensing effect. The at least one addressable optical element is adapted for changing the transmittance of at least one of the plurality of regions in response to a control signal. The at least one addressable optical element may be adapted for changing the ratio of the intensity of light transmitted through this at least one region over the intensity of light incident on the at least one addressable optical element. Particularly, the at least one addressable optical element may be adapted for changing the ratio of the fraction of light transmitted through a first region of the plurality of regions over the fraction of light transmitted through a second region of the plurality of regions. The at least one addressable optical element may be a non-concentric area. The non-concentric area may be a non circle-symmetric sector of the optical element with lensing effect. The non-concentric area may comprise one or more sector regions of the optical element with lensing effect. The one or more sector regions may be pie-slice shaped, e.g. having their pie-point in the center of the optical element with lensing effect. The optical lens device also comprises a control means for generating the control signal, e.g. for generating the control signal in order to select a focal length or combination, e.g. superposition, of focal lengths from the focal lengths provided by the plurality of regions, for example, to select a dioptre or optical correction.

The optical lens device according to embodiments of the present invention may be adapted for use as an ophthalmic contact lens or for use as an intra-ocular implant. For example, a multifocal contact lens can be provided in accordance with embodiments of the present invention that comprises addressable optical elements which may be incorporated in the lens for selectively blocking or transmitting light through different zones of the lens. Thus, these different zones can provide different eye corrections, e.g. different dioptric powers. It is an advantage of such embodiments of the present invention that an efficient and simple means for real-time adjustment of the diopter of an ophthalmic lens is provided, e.g. without requiring complex elements, e.g. active lens elements with an adjustable shape and/or adjustable refractive index. An ophthalmic lens according to embodiments of the present invention may be suitable for correcting nearby and far vision accommodation, e.g. to overcome the effects of presbyopia. However, other lens corrections such as, but not limited to, astigmatic correction can also be implemented in a device according to embodiments of the present invention.

For example, for an optical lens device intended for use as a contact lens, modern materials known in the art for either soft or rigid gas permeable contact lenses may be used as base material for the element with lensing effect to provide good biocompatibility and a sufficiently high oxygen transmissibility. It is an advantage of simple designs, e.g. the embodiment illustrated in FIG. 9 and FIG. 10, that few electro-optic components and supporting electronic elements need to be provided on or embedded in such biocompatible substrate. Therefore, a good trade-off may be achieved between an acceptable oxygen transmissibility and a good multifocal functionality. The element with lensing effect may furthermore be provided with a suitable coating for improving the properties of the device for use as a contact lens, for example, may be provided with a parylene coating, although embodiments are not limited thereto.

However, an optical lens device according to embodiments of the present invention may also be suitable for other fields of application, e.g. for use in an optical apparatus such as a photographic camera. Thus, embodiments of the present invention may advantageously enable the switching of the optical apparatus, e.g. the photographic camera, between different focal distances, e.g. for zooming and focusing, without requiring mechanically moving parts, e.g. moving lens groups.

Figure 2:
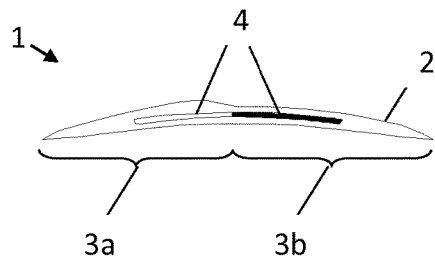
FIG. 2 shows a transversal view of the optical lens device shown in FIG. 1, according to embodiments of the present invention.

FIG. 1 and FIG. 2 show an optical lens device 1 according to embodiments of the present invention. FIG. 1 shows a frontal view of such optical lens device 1, while FIG. 2 shows a transversal view, e.g. a cross-sectional view, of the optical lens device 1. The optical lens device 1 comprises an element with lensing element 2. In particular embodiments, the element with lensing effect 2 may be a lens, such as a circularly shaped lens. However, a lens having another rounded shape, a rectangular shape or any other shape may also be within the scope of embodiments of the present invention, as will be understood by the person skilled in the art. The element with lensing effect may be composed of a rigid gas permeable or soft material, e.g. a material as is known in the art as a suitable material for lenses, e.g. for contact lenses.

The element with lensing effect 2 comprises a plurality of regions, for example two regions 3a,3b, although more than 2 regions, such as for example 3, 4 or more regions also can be implemented. Each such region 3a,3b has a corresponding refractive power for providing a corresponding focal length distinct from the focal length of at least another region of the plurality of regions, e.g. each region may have a distinct refractive power and may thus provide a corresponding distinct focal length. The shape of these regions, e.g. of these individually selectable lens zones, may not be limited to a specific arrangement, but may depend on design considerations for a particular application.

Figure 3:
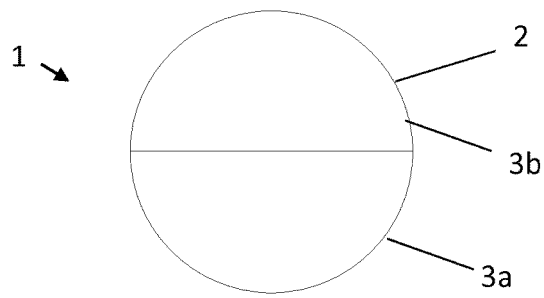
FIG. 3 shows a simple illustrative embodiment of an optical lens device according to embodiments of the present invention.
Figure 4:
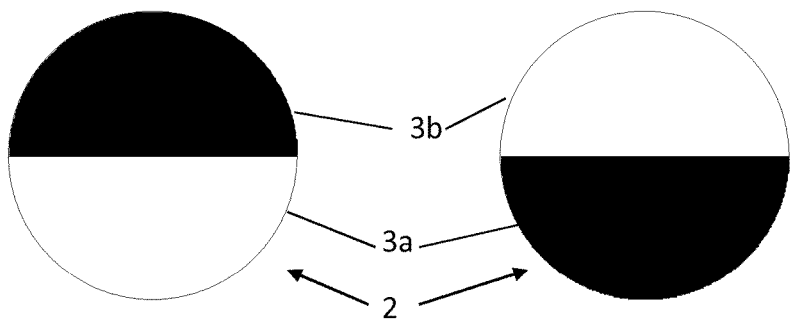
FIG. 4 illustrates the selection of a first focus in the optical lens device shown in FIG. 3, according embodiments of the present invention.
Figure 5:
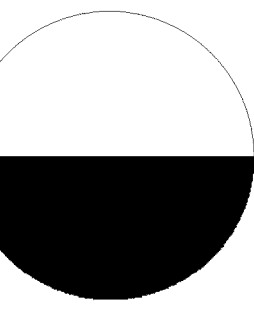
FIG. 5 illustrates the selection of a second focus in the optical lens device shown in FIG. 3, according embodiments of the present invention.

The element with lensing effect can be constructed in such a way that the different regions may have different optical powers. For example, FIG. 3 shows a simple illustrative embodiment where the element with lensing effect 2, e.g. an optical lens, comprises two regions that together constitute the whole element area. For example, in a contact lens, the first region 3a may be constructed in such a way that it corrects the vision for nearby vision while the second region 3b may correct the vision for remote vision. By making region 3a substantially transparent and region 3b substantially opaque, as shown in FIG. 4, light entering the eye of the wearer will only be corrected for nearby vision and the wearer will have sharp vision of nearby objects. Conversely, by making region 3a opaque and region 3b transparent, as shown in FIG. 5, the lens wearer will have essentially a sharp remote vision. The different optical behavior of the two regions may be established by having different lens curvatures in these two regions, e.g. a different curvature on the front side and/or on the back side of the refractive element 2, for example as shown in FIG. 2. Furthermore, the transition between such regions may constitute a discontinuity of the lens surface. However, in accordance with embodiments of the present invention, a smooth transition may be provided between adjacent regions 3a,3b. Furthermore, a narrow opaque zone may be optionally arranged between addressable optical elements corresponding to the adjacent regions 3a,3b, e.g. an opaque zone having a width sufficient for masking such a smooth transition zone. It is an advantage of such smooth transition that unwanted effects due to sharp edges on the surface of the lens are avoided or reduced, e.g. hampering of the eye lid movement for a contact lens.

Figure 6:
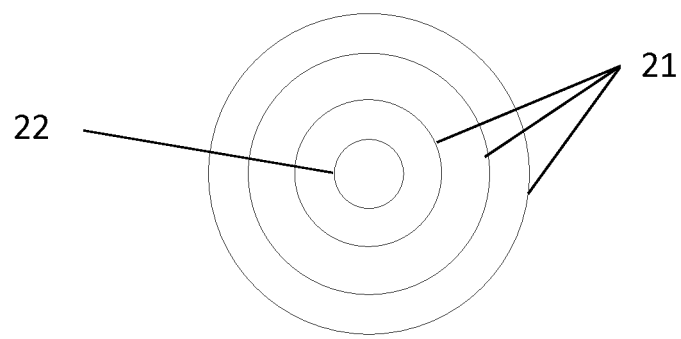
FIG. 6 shows a concentric arrangement of regions of the element with lensing effect of an optical lens device according to a first exemplary embodiment of the present invention.
Figure 7:
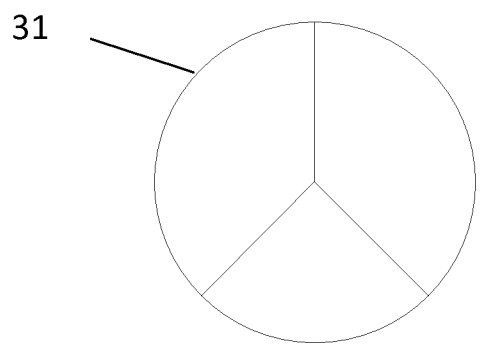
FIG. 7 shows a sectorial arrangement of regions of the element with lensing effect of an optical lens device according to a second exemplary embodiment of the present invention.
Figure 8:
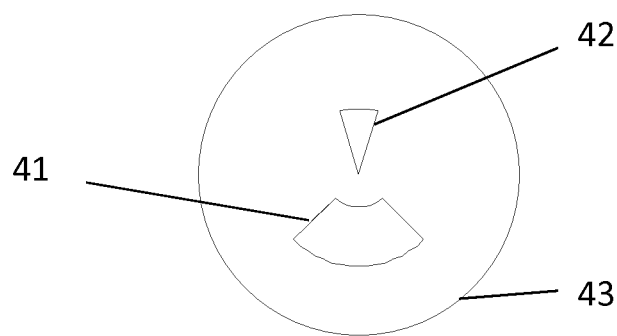
FIG. 8 shows an optical lens device according to embodiments of the present invention in which the total area spanned by the at least one addressable optical element is smaller than the surface area of the element with lensing effect.

Two exemplary possible arrangements for the regions of the element with lensing effect 2, in accordance with advantageous embodiments of the present invention, are shown in FIG. 6 and FIG. 7, which are further discussed hereinbelow. However, other arrangements or shapes of the areas may also fall within the scope of the present invention, one example thereof being as shown in FIG. 8, and such arrangements or shapes of the area may be chosen appropriately for a particular intended application, as will be understood by the person skilled in the art.

Although the different optical power regions may be created using refractive optics with different surface curvatures, such regions may also be implemented using other effects. For example, a material with a gradient in the refractive index may be used in order to achieve refraction and locally varying focal length without introducing surface curvature. For example, the element with lensing effect 2 may be a gradient index (GRIN) lens. It is an advantage of such gradient index lenses that the regions having different dioptric power can be juxtaposed without a discontinuity in the shape of the lens surface.

Alternatively or in addition thereto, the element with lensing effect 2 may comprise a diffractive optical element, for example the element with lensing effect 2 may be implemented by introducing microscopic topology into the topology of the lens, e.g. by providing microgrooves therein. In fact, any method or combination of methods that allow to produce a lens with different lensing characteristics in different zones may be suitable for manufacturing an optical lens device according to the present invention.

The optical lens device 1 comprises at least one addressable optical element 4 integrated in or provided on the element with lensing effect 2. For example, the at least one addressable optical element may be embedded into the element with lensing effect, e.g. embedded in the lens such as shown in FIG. 2, or may be placed in close proximity to the element with lensing effect, e.g. arranged on the lens. A one-on-one correspondence may exist between the addressable optical elements and the plurality of regions of the element with lensing effect, e.g. forming selectable lens zones.

The shape and arrangement of the at least one addressable optical element 4 may be determined by the shape and arrangement of the plurality of regions of the element with lensing effect. For example, the at least one addressable optical element may be arranged such as to provide at least one selectable lens zone corresponding to at least one region of the element with lensing effect.

However, the union of all selectable zones, e.g. the total area spanned by the at least one addressable optical element may be smaller than the surface area of the element with lensing effect, e.g. the at least one addressable optical element may not entirely cover the element with lensing effect. For example, FIG. 8 shows an arrangement in which regions 41 and 42 of the element with lensing effect are provided with a corresponding addressable optical element, while region 43 of the element with lensing effect is not provided with an addressable optical element.

It is to be noted that the at least one addressable optical element may be adapted for changing the ratio of the fraction of light transmitted through a first region of the plurality of regions over the fraction of light transmitted through a second region of the plurality of regions. Therefore, if the cardinality of the regions of the element with lensing effect equals N, N−1 addressable optical elements may suffice to adjust all pairwise transmission ratios for the N regions. The non-addressable zones, e.g. corresponding to the region 43 in the example shown in FIG. 8, may be permanently transparent, permanently opaque or have any transmission coefficient between 0 and 100%. This transmission may even be location dependent, so that gradual transmission patterns are possible. Thus, any static transmission pattern may be implemented in the non-addressable zones of the lens.

Figure 9:
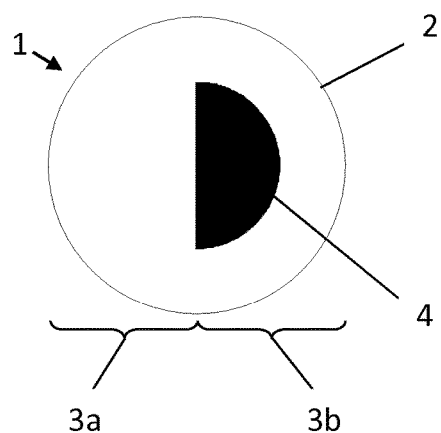
FIG. 9 shows an optical lens device according to embodiments of the present invention, which comprises only a single addressable optical element.
Figure 10:
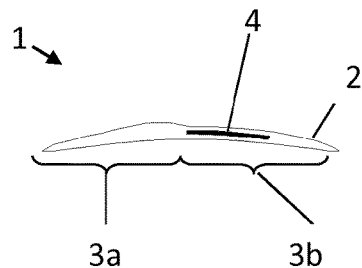
FIG. 10 shows a transversal view of the optical lens device shown in FIG. 9, according to embodiments of the present invention.

For example, in FIGS. 9 and 10 an exemplary embodiment is shown, similar to the optical lens device shown in FIG. 1 and FIG. 2, but which comprises only one addressable optical element 4. Because the addressable optical element 4 only covers half of the lens, e.g. the right side as shown in FIG. 9, any absorption in the transparent state, for example due to polarization or other causes of sub-optimal behavior of the addressable optical element, is avoided for the other half, e.g. the left side of the lens. Such optical device may enable the selection of a single focus, corresponding to the focus of the left region 3a, by blocking light transmission through the right region 3b via the addressable optical element 4, and the selection of a dual focus, e.g. a superposition of the focus of the left and right regions 3a,3b, by allowing light transmission through the right region 3b via the addressable optical element 4. The situation For example, light transmitted in the latter configuration may be partly corrected for remote vision and partly for nearby vision. Although this has the disadvantage of reduced contrast and ghost imaging, as would be the case in a conventional dual focus lens; the system may have an advantageously high optical transmission and is simple to implement since only one addressable optical element 4 has to be addressed. For applications where it is sufficient to have one high-contrast state, this embodiment could be preferable.

Furthermore, the at least one addressable optical element 4 may comprise overlapping addressable zones. For example, two or more layers of addressable optical elements may be provided.

The at least one addressable optical element 4 is adapted for changing the transmittance of at least one of the plurality of regions in response to a control signal. Thus, light may be selectively allowed to pass through one or more lens zones in accordance with the control signal. Each such region 3a,3b has a corresponding refractive power for providing a corresponding focal length, therefore, a focus, or combination of superimposed focuses, may be selected by substantially enabling or preventing the transmission of light through at least one of the plurality of regions in response to the control signal.

The transmission of the at least one addressable optical element 4 may be selected in a range between a minimum transmittance value and a maximum transmittance value. The minimum value may be 0% or low enough for the intended application, for example 5% or 10%, or even 20%. The maximum value may be 100% or high enough for the intended application, e.g. 95% or 70%, or even 40%.

The transmission of each of the at least one addressable optical element 4 may be selected from a discrete number of values in this range, e.g. the transmission can be set to either 0% or 100%, or either 5% or 95%, or may be set to 0%, 50% or 100%. In embodiments of the present invention, the transmission of the at least one addressable optical element may even be selected from a continuity of intermediate states between the minimum and the maximum transmittance value.

Each addressable optical element 4 may be implemented in such a way that the transmission inside the addressable zone covered by the addressable optical element is essentially uniform. However, in embodiments according to the present invention, an addressable optical element may also provide a transmission gradient. For example, such optional transmission gradients may be realized by incorporating a fixed transmission pattern covering the addressable zones, but may also be the result of a non-uniform operation of the addressable optical elements.

The at least one addressable optical element 4 may comprise a liquid crystal (LC) technology element, such as, but not limited to, a guest-host LC, twisted nematic LC, vertically aligned nematic LC, hybrid aligned nematic LC, in-plane-switching LC, ferroelectric LC or antiferroelectric LC element. The LC technology element can make use of polarization effects or not. It is an advantage of a non-polarization based LC technology element, such as a guest-host LC element, that a high maximum transmission can be achieved.

The at least one addressable optical element may also be based on other electro-optical effects for switching, e.g. with a discrete number or a continuity of intermediate degrees, between substantially transparent and substantially opaque. For example, the at least one addressable optical element may comprise an element using electrochromic behavior or electrowetting. Furthermore, the at least one addressable optical element may comprise an element exhibiting a non-electrically addressable effect, such as, but not limited to, pressure-sensitive light transmission elements or temperature-driven variable transmission elements.

In particular advantageous embodiments, the at least one addressable optical element may be bistable or multistable, such that energy is only needed to change the transmission state, e.g. no energy is expended for maintaining the existing transmission state.

The at least one addressable optical element may comprise a power supply. For example the at least one addressable optical element may comprise an external power connection, e.g. the energy to power the addressable optical elements may be provided by an electrical connection. The addressable optical element may comprise an integrated battery system, an integrated energy-harvesting or scavenging system or may receive power via wireless transmission of energy, e.g. using radio frequency radiation, inductive coupling, light or another wireless carrier of energy. Furthermore, a combination of such means for power supply may also be used, e.g. a battery system that can be recharged using an inductive energy coupling system.

FIG. 6 shows an arrangement of the regions of the element with lensing effect of an optical lens device according to a first exemplary embodiment in one aspect of the present invention. In this exemplary embodiment, the plurality of regions of the element with lensing effect may comprise regions arranged as concentric rings 21, e.g. concentric around the central optical axis of the element with lensing effect. Furthermore, the plurality of regions of the element with lensing effect may comprise the central circular zone 22. Such arrangement may be known in, for example, contact lens design, e.g. to produce static multifocal lenses. Therefore, the element with lensing effect may be a static multifocal lens, e.g. an ophthalmic multifocal lens as known in the art.

For application of the optical lens device according to this embodiment in a contact lens, it is noted that, under bright circumstances, the eye pupil has a small diameter. Although the pupil may be separated from the lens by a few millimeters, the central region of the lens may primarily contribute to the vision under such bright circumstances. In dim lighting circumstances, the pupil has a larger diameter, and the contribution of the outer rings may become relatively more important than that of the central part of the lens.

However, without the active shading provided by the present invention, a similar concentrically arranged multifocal lens would depend on a functional relationship between the perceived brightness and the appropriate focal distance. The present invention overcomes this limitation by incorporating at least one addressable optical element which enables to effectively select the active lens regions, independent of the brightness level. For example, the at least one addressable optical element may comprise one or more concentric elements, e.g. concentric annular elements optionally including a central circular element, arranged such as to correspond to the concentric ring regions 21 or central regions 22 of the element with lensing effect.

Therefore, it is an advantage of embodiments of the present invention that focus selection can be achieved in a contact lens without assuming a brightness-focal distance relationship. It is furthermore an advantage that a default mode of operation may involve using such contact lens in a passive mode, in which pupil dilation can select a default focus as is known for static multifocal contact lenses. However, if the user perceives an incorrect focus selection, e.g. while attempting to read a book under very bright conditions, or while observing a panoramic view under dim lighting conditions, the user can operate the control means in order to select the correct focus in accordance with embodiments of the present invention. Therefore, embodiments provide the further advantage of enabling a power efficient focus selection when combining a passive default mode with a powered, active focus selection for correcting the default. This furthermore has the advantage of requiring little user intervention, e.g. only requiring a control command when the default focus corresponding to the conventional passive multifocal lens operation is not suitable.

Even though the varying pupil diameter may reduce the effectiveness of the outer zones in an optical lens device arranged as shown in FIG. 6, e.g. the outer zones can only contribute to image formation in dim lighting circumstances, this may be overcome by normal pupil dilation. Since incident light can be blocked at the center if one of the outer regions is actively selected in accordance with embodiments of the present invention, this can cause the pupil to dilate in response, such that the outer zones can contribute as intended to the image formation.

FIG. 7 shows an optical lens device according to a second exemplary embodiment of the present invention. Here, the regions of the element with lensing effect may comprise at least one lens sector 31. Embodiments in accordance with such arrangement have the advantage of being insensitive to a diaphragm selection, e.g. to the variable pupil diameter for an ophthalmic contact lens, since each region extends substantially to the optical center of the element with lensing effect, e.g. each sector has a tip positioned inside the smallest possible pupil area.

Figure 11:
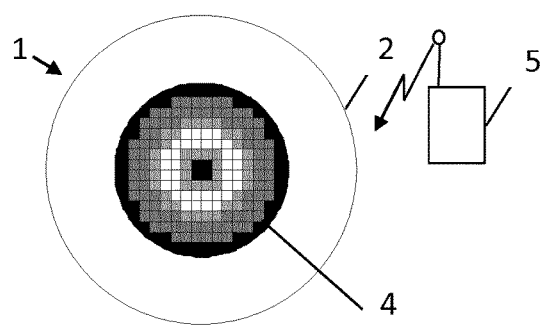
FIG. 11 shows a device according to another embodiment of the present invention, having an aspheric multifocal design and an array of addressable optical elements.
Figure 12:
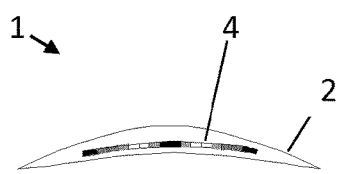
FIG. 12 shows a transversal view of the optical lens device shown in FIG. 11, according to embodiments of the present invention.

In FIG. 11, another embodiment according to the present invention is shown. Here, an aspheric multifocal design is illustrated, in which the optical transmission across the entire element with lensing effect 2 can be tuned by the incorporation of an array of addressable optical elements 4. The optical lens device is provided with a rectangular array of addressable elements as shown, similar to a matrix display device, with which an arbitrary transmission pattern can be established within the resolution limits provided by this array. The element with lensing effect 2 may be an aspheric multifocal lens, e.g. as shown in FIG. 12. Here, a continuously varying refractive power and corresponding focal length are provided by an aspheric curvature of the lens surface. Thus, any local neighbourhood of a point on the element with lensing effect 2 constitutes a region having a corresponding refractive power for providing a corresponding focal length distinct from the focal length of another region, e.g. a local neighbourhood of a different point on the element with lensing effect 2. In other words, the element with lensing effect 2 may comprise an uncountable plurality of regions, each region having a corresponding refractive power for providing a corresponding focal length distinct from the focal length of at least one other region of said plurality of regions.

Figure 13:
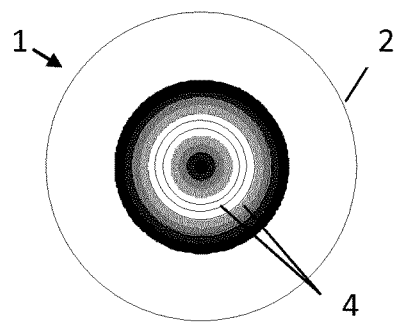
FIG. 13 shows an optical lens device according to embodiments of the present invention comprising addressable optical elements arranged in concentric addressable rings.
Figure 14:
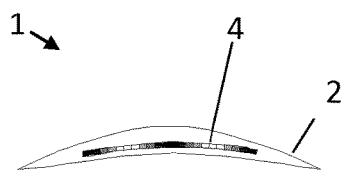
FIG. 14 shows a transversal view of the optical lens device shown in FIG. 13, according to embodiments of the present invention.

FIG. 13 shows an optical lens device 1 comprising addressable optical elements 4 arranged in concentric addressable rings. Therefore, such device allows the selection of any axial-symmetric transmission pattern. The optical lens device further comprises, similarly to the previous example in FIG. 11 and FIG. 12, an aspheric element with lensing effect 2, e.g. shown in FIG. 14, having a varying optical power as a function of the distance from the center point. For example, the device may focus on a near, middle or far point depending on where the light transmission is allowed. In addition, more complex patterns can be applied by administering a gradient in the transmission in the lens. This can easily be implemented if the optically addressable elements can have intermediate transmission states. Thus, a detailed balance can be achieved between image formation of nearby, medium distance or distant features. Moreover, by tuning the overall transmittance of the lens, the pupil size can be affected and pupil size induced blur can thus be minimized. This principle can also be applied to different embodiments, as will be apparent to the person skilled in the art.

An optical lens device according to embodiments of the present invention also comprises a control means 5 for generating the control signal for the least one addressable optical element. This control signal may be transmitted through a conductive path, e.g. the control means may be provided in or on the element with lensing effect by, for example, semiconductor processing, and may be connected to the at least one addressable optical element via an integrated connection, e.g. as shown in FIG. 1. Alternatively, the control means may communicate wirelessly with the at least one addressable optical element, e.g. via radio frequency transmission or via optical signaling, e.g. as illustrated in FIG. 11.

In embodiments where the control means is integrated in or on the element with lensing effect, such control means may receive commands via eye lid gestures or pressure signals provided via the closed eyelid. For example, such commands may comprise blinking 2 times within 1 second, keeping the eye closed for 1 second or pressing on the lens through the closed eyelid. The control means may comprise a sensing circuit inside the lens for detecting such gestures and control the addressable optical elements accordingly.

The processing of the input data and determination of the appropriate command of the optical elements can be performed by an integrated electronic circuit, although embodiments of the present invention are not limited thereto. This circuit can be made using thin-film technology or silicon technology. In the latter case, the silicon chip can be embedded into or onto the lens using techniques such as, or similar to, ultra-thin chip packaging (UTCP). In the former case, the circuit can be integrated on the same carrier substrate as the addressable optical elements or on another, dedicated, carrier substrate that can be integrated into or onto the lens together with the optical elements.

Particularly, in the case of bistable or multistable addressable optical elements, the control means may comprise an external power source, which when brought into an effective range of power transmission, e.g. via induction, triggers a state change of the bistable or multistable addressable optical elements. It is an advantage of such embodiments, and particularly of such embodiments comprising only a single addressable optical element, that the control circuitry required in or on the element with lensing effect can be simple, robust and low cost.

Figure 15:
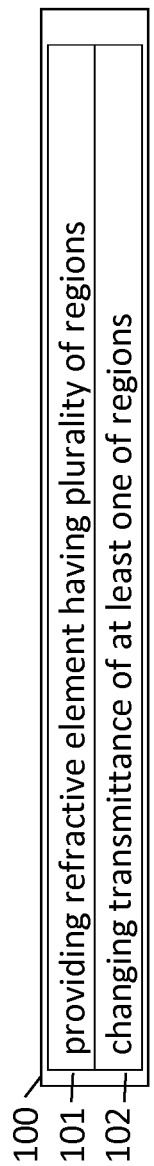
FIG. 15 illustrates an exemplary method according to embodiments of the present invention.

In a second aspect, the present invention relates to a method 100 for controlling the focal length of an optical lens device, e.g. advantageously an optical lens device 1 according to the first aspect of the present invention. An exemplary method 100 according to this second aspect of the invention is illustrated in FIG. 15. This method 100 comprises providing 101 an element with lensing effect 2 comprising a plurality of regions 3a,3b, in which each region has a corresponding refractive power for providing a corresponding focal length distinct from the focal length of at least one other region of the plurality of regions. The method further comprises changing 102 the transmittance of at least one of the plurality of regions by controlling at least one addressable optical element 4 integrated in or provided on the element with lensing effect 2. Details with respect to such an exemplary method will be clear to the person skilled in the art in the light of the description of the first aspect of the present invention provided hereinabove. Moreover, such a method may comprise steps expressing the functionality of devices, components and/or arrangements of devices according to embodiments of the present invention.

The present invention also relates to the use of an optical lens device 1 according to the first aspect of the present invention for human vision correction, e.g. as contact lens or intra-ocular implant. For example, the present invention also relates to the use of an optical lens device 1 according to the first aspect of the present invention for correction of presbyopia.

In a further aspect, the present invention also relates to an optical lens device having the same features as described for the optical lens device of the first aspect, but restricted by its surface area. The at least one addressable optical element has a lens surface area being at least 10%, e.g at least 15%, e.g. at least 20% of the surface area of the optical element with lensing effect. The shape thus may be any suitable shape such as for example, one or more sectors, a concentric shape e.g. one or more concentric rings, a disc shape, etc. Other features thus may be as described in any of the earlier discussed embodiments.

The invention claimed is:

1. An optical lens device having an actively controllable focal length, comprising:
    an element with lensing effect comprising a plurality of regions, each region having a corresponding refractive power arranged for providing a corresponding focal length distinct from the focal length of at least one other region of said plurality of regions;
    at least one addressable optical element integrated in or provided on the element with lensing effect, the at least one addressable optical element being arranged for changing the transmittance of at least one of said plurality of regions in response to a control signal; and
    a control means programmed for generating said control signal,
    wherein said at least one addressable optical element is non-concentric, said at least one addressable optical element comprising an addressable optical element configured as one or more sectors of the element with lensing effect,
    wherein the one or more sectors are pie-slice shaped sectors with their pie-point at the centre of the element with lensing effect.

2. An optical lens device according to claim 1, wherein said optical lens device is adapted for use as an ophthalmic contact lens or an intra-ocular implant.

3. An optical lens device according to claim 1, wherein the shape and arrangement of the at least one addressable optical element is determined by the shape and arrangement of the plurality of regions of the element with lensing effect.

4. An optical lens device according to claim 1, wherein a corresponding addressable optical element is provided in or on each of said plurality of regions.

5. An optical lens device according to claim 1, wherein said element with lensing effect is made of rigid gas permeable or soft material.

6. An optical lens device according to claim 1, wherein said at least one addressable optical element comprises a surface area of at least 10% of the surface area of the element with lensing effect.

7. An optical lens device according to claim 1, wherein said at least one addressable optical element covers an area which is substantially less than the total area of the element with lensing effect.

8. An optical lens device according to claim 1, wherein said at least one addressable optical element comprises overlapping layers.

9. An optical lens device according to claim 1, wherein said at least one addressable optical element comprises a liquid crystal technology element.

10. An optical lens device according to claim 1, wherein said at least one addressable optical element comprises a bistable or multistable element.

11. An optical lens device according to claim 1, wherein the at least one addressable optical element comprises an energy supply.

12. The use of an optical lens device according to claim 1 for human vision correction.

13. A method for controlling the focal length of an optical lens device, comprising:
   providing an element with lensing effect comprising a plurality of regions, each region having a corresponding refractive power for providing a corresponding focal length distinct from the focal length of at least one other region of said plurality of regions; and
   changing the transmittance of at least one of said plurality of regions by controlling at least one addressable optical element integrated in or provided on the element with lensing effect, said at least one of said plurality of regions,
   wherein the at least one sector shape is a pie-slice shaped sector with its pie-point at the centre of the element with lensing effect.

* * * * *